United States Patent [19]

Koizumi et al.

[11] 4,202,628

[45] May 13, 1980

[54] FLAMELESS ATOMIZER

[75] Inventors: Hideaki Koizumi; Kazuo Moriya, both of Katsuta, Japan

[73] Assignee: Hitachi, Ltd., Japan

[21] Appl. No.: 781,938

[22] Filed: Mar. 28, 1977

[30] Foreign Application Priority Data

Mar. 29, 1976 [JP] Japan .................................. 51-33668

[51] Int. Cl.² ............................................... G01J 3/30
[52] U.S. Cl. ........................................ 356/312; 356/244
[58] Field of Search ........................... 356/85, 244, 312

[56] References Cited

U.S. PATENT DOCUMENTS

| 3,862,805 | 1/1975 | Tamm et al. | 356/244 |
| 4,098,554 | 7/1978 | Huber et al. | 356/244 |

FOREIGN PATENT DOCUMENTS

| 2155407 | 5/1973 | France | 356/244 |
| 1385791 | 2/1975 | United Kingdom | 356/85 |

OTHER PUBLICATIONS

"Modification of a Graphite Tube Atomizer for Flameless Atomic Absorption Spectrometry"; Issaq et al.; Analytical Chemistry, vol. 47, #13, Nov. 75, pp. 2281-2283.

*Primary Examiner*—Vincent P. McGraw
*Attorney, Agent, or Firm*—Craig & Antonelli

[57] ABSTRACT

A cuvette used in a flameless atomizer is hollow and includes an opening at both ends and a hole in a radial direction substantially at its central portion. The cuvette is made of a conductive material and Joule-heated by currents flowing therethrough. The interior of the cuvette is divided substantially into three sections: a sample mount section at which a sample introduced through the hole of the cuvette is disposed; a light beam path section through which light incident from the opening at one end of the cuvette passes and goes out of the opening at the other end; and an absorption cell section at which the light beam path section intersects with atomic vapors generated from the sample disposed at the sample mount section. The electric resistance of the cuvette is made smaller at the sample mount section than at a portion near the absorption cell section. This allows the higher temperature of the portions near the absorption cell section than that of the sample mount section. Therefore, almost all of the atomic vapors in the cuvette exist at the absorption cell portion, and the application of a magnetic field to the absorption cell section allows a great improvement in analysis precision and sensitivity of the flameless atomizer for atomic absorption analysis using a Zeeman effect.

15 Claims, 9 Drawing Figures

FLAMELESS ATOMIZER

The present invention relates to a flameless atomizer and more particulary to a flameless atomizer suitably adapted for use in an atomic absorption analysis, atomic fluorescence analysis, and further Zeeman atomic absorption analysis.

The flameless atomizer in the prior art includes two electrodes between which a hollow-cylindrical cuvette is supported. The supply of the cuvette with a current from the electrodes causes a Joule-heating of the cuvette. A sample introduced into the cuvette is atomized by the Joule-heating. The conventional cuvette is formed to be cylindrical with a constant thickness, and therefore with electric resistance uniform on each portion thereof. The electrode has a sufficiently small electric resistance as compared with the electric resistance of the cuvette. For this reason, the cuvette is Joule-heated with its temperature distributed to be at the highest on its central portion and smaller near the electrode, as a result, the atomic vapor atomized near the central portion is condensed or recombined on the wall of the cuvette at its periphery having the smaller temperature. This leads to the poor reproducibility of the analysis.

The application of a magnetic field to the atomic vapor, on the other hand, causes the split of absorption spectral lines due to the Zeeman effect. Some of the atomic vapors dispersed into the cuvette by thermal diffusion are subjected to the Zeeman effect by the magnetic field and the others are not subjected thereto. A small amount of the atomic vapors subjected to the Zeeman effect results in the reduced sensitivity of analysis. Further, the atomic vapors not subjected to the Zeeman effect cause the reduction of the analysis precision because they act to produce errors of the analysis.

It is an object of the present invention to provide a flameless atomizer capable of obtaining analysis values with good reproducibility.

It is another object of the present invention to provide a flameless atomizer with an improved precision of measurement even in use in the atomic absorbtion analysis using the Zeeman effect.

The present invention is intended to provide a flameless atomizer in which a sample mount on which a sample to be analyzed is placed has a smaller temperature than its adjacent portions.

Figure 1:
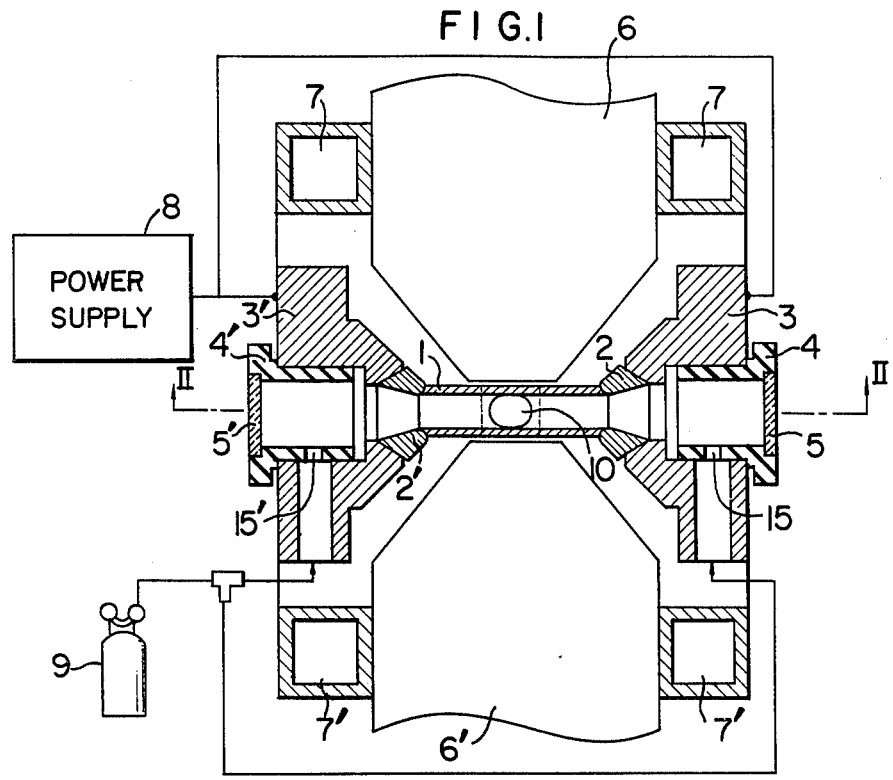
FIG. 1 is a cross section showing one embodiment of a flameless atomizer according to the present invention.
Figure 2:
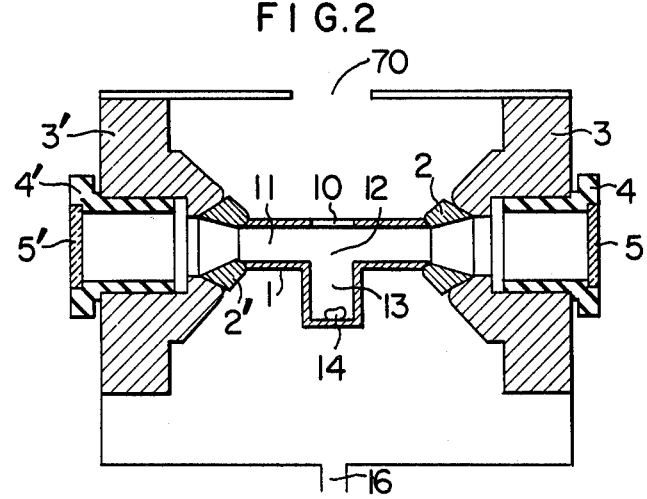
FIG. 2 is a section taken along a line II—II in FIG. 1.

FIG. 1 is a cross section of one embodiment of a flameless atomizer according to the present invention, and FIG. 2 is a section along a line II—II in FIG. 1. A cuvette 1 is fixedly supported by means of electrodes 3, 3' through cuvette cones 2, 2'. The cuvette cones 2, 2' are made of a conductive material such as graphite. The cuvette 1 has a T-shaped section and includes a light beam path section 11, an absorption cell section 12, and a sample mount section 13, depending upon its nature. The cuvette 1 is open at both ends to pass light incident from an opening at its one end through the light beam path section 11 to an opening at the other end. A sample to be analyzed is introduced from a sample introduction port 10 into the sample mount section. The absorption cell section 12 is a section at which the atomic vapors of the sample intersect with the light passing through the light beam path section 11. The cuvette 1 is supplied with AC or DC current from a power supply 8 through the electrodes 3, 3' and the cuvette cones 2, 2'. Magnets 6, 6' are so provided that they sandwich the absorption cell section 12 of the cuvette 1 at their both ends. Cooling water is caused to flow through cooling water pathes 7, 7' to keep the temperature of the magnets constant. The electrodes 3, 3' are provided with gas flow adjustment portions 4, 4', which respectively include light transparent windows 5, 5' and holes 15, 15' into which a protective gas flows from a bombe 9.

A sample 14 to be analyzed is introduced from the sample introduction port 10 to the sample mount section 13. The supply of current from the power supply to the cuvette 1 causes the cuvette 1 to be heated by Joule-heating. This causes the elevation of the temperature at the sample mount section 13 and the atomization of the sample 14 into atomic vapors. In general, the heating is effected through three steps: the first step in which the sample is heated for drying up to about 100° C. and the water in the sample is converted into vapor; the second step in which the sample is heated for carbonization to several hundreds °C., and organic materials, dusty particles, acids, etc., coexisting in the sample other than elements for analysis objects are pyrolyzed into smoke; and the third step in which the sample is heated for atomization to about 2,000°–3,000° C. It is to be noted that the sample mount section of the cuvette 1 is constructed to have a projection. This allows the smaller electric resistance of the sample mount section 13 and the lower temperature than the absorption cell section 12. This further allows the great thermal diffusion because of the great area of this section. As a result, the temperature of the sample mount section 13 is lower by about 100° C. than that of the circumference of the absorption cell section. Thus, no atomic vapor atomized at the sample mount section is condensed or recombined on the wall surface of the cuvette near the absorption cell section with the result of improved reproducibility of analysis.

Further, the sample introduction port 10 above the absorption cell 12 has an inner diameter which is sufficiently great and substantially the same as the inner diameter of the sample mount section 13. This allows the atomic vapor atomized at the sample mount section 13 to rise through the absorption cell section 12 and go out of the cuvette 1 through the sample introduction port 10. No atomic vapor moves towards the openings at both ends of the cuvette 1 from the absorption cell section 12. Thus, the application of the magnetic field to the absorption cell section 12 by means of the magnets 6, 6' causes the atomic vapor in the interior of the absorption cell section 12 to be subjected to the Zeeman effect with its absorption spectrum split. Almost all of the atomized vapors are subjected to the Zeeman effect with the result of the improvement in analysis precision and sensitivity.

The temperature of the absorption cell section 12 is greater than that of the sample mount section 13. This also applies for the case that the sample mount section 13 has the constant temperature and the sample is vaporized in the form of molecules, so that the absorption cell section 12 has much higher temperature at this time. The molecular sample can, therefore, be atomized quite satisfactorily.

The inactive gas supplied from the bombe 9 serves as a protective gas and carrier gas. The cuvette 1 of graphite suffers from thermal damages by oxygen in the atomsphere of surroundings when it becomes at high temperature. This requires the isolation from the air and the generation of the atmosphere of the inactive gas. The inactive gas introduced from both the ends of the cuvette 1 coexisting scattering particles produced at the step of carbonizing the sample to be exhausted out of the cuvette 1. Helium or nitrogen is used as the inactive gas in addition to argon. The inactive gas introduced from both the ends of the cuvette 1 not only produces the atmosphere of the inactive gas through the interior of the cuvette 1, but exhausts impurities through the sample introduction port 10 out of the cuvette 1. Further, the inactive gas introduced from the port 16 produces the atmosphere of the inactive gas in the circumference of the cuvette 1, and is exhausted through an exit 70.

The magnets 6, 6' are disposed at right angles with respect to a direction of the light beam path 11 and a direction along which the atomic vapors rise. For this reason, the atomic vapor heated within the cuvette 1 goes upwards vertically without any contact with the magnets 6, 6'. It is general that the magnet has a thermal coefficient with its magnetic field varying in dependence upon the temperature. In the present invention under application, however, the atomic vapor heated does not come into contact with the magnets 6, 6', so that the magnetic field is stabilized. More preferably, the magnet is cooled by the cooling water with its temperature kept constant. This results in no fluctuation of the magnetic field and improvement in analysis precision.

Figure 3:
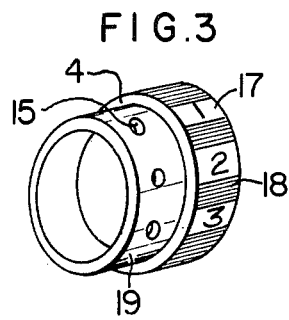
FIG. 3 is a perspective view showing a gas flow adjustment portion used in the flameless atomizer in FIG. 1.

The carrier gas flows through the hole 15 of the gas flow adjustment portion 4 into the cuvette 1. The gas flow adjustment portion 4, shown more fully in FIG. 3, includes a grip portion 18 provided with signs 17. A flow adjustment portion 19 includes a plurality of holes 15 each having a different diameter corresponding to the signs 17, respectively. The gas flow adjustment portion 4 is rotatably mounted on the electrode 3. Thus, the turning of the gas flow adjustment portion 4 with reference to the sign 17 makes it possible to adjust the flow of the gas carrier stepwise. A gas flow adjustment portion 4' is constructed similarly to the gas flow adjustment portion 4. The flow adjustment of the carrier gas is changed depending upon the sample. In the prior art, a flow meter is used to effect the continuous adjustment of the flow. It is, however, difficult to maintain the flow always constant and accurate, as a result, the poor reproducibility of the analysis is caused. According to the present invention, however, the flow of the carrier gas can be stepwise changed always accurately and easily, so that the reproducibility of the analysis is improved.

Figure 4:
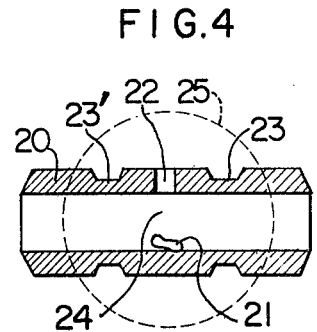
FIG. 4 is a cross section of another embodiment of a cuvette according to the present invention.

FIG. 4 is a cross section showing another embodiment of a cuvette according to the present invention. A cuvette 20 includes a sample introduction port 22 for introducing a sample 21. The sample introduction port 22 is provided at both ends with high temperature heating recesses 23, 23', which has a reduced thickness radially of the cuvette 20 to provide the greater electric resistance than the other portions of the cuvette 20. Thus, the cuvette 20 has the temperature distributed to be the highest at a portion near the sample introduction port 22; the second highest at a portion near the high temperature heating necesses 23, 23'; and the lowest at a portion at which the sample 21 is disposed. This temperature distribution causes the atomic vapor from the sample to be sealed within an absorption cell section 24. Therefore, the application of a uniform magnetic field 25 so as to cover the absorption cell portion 24 allows the improvement of the analysis precision and sensitivity. Moreover, no atomic vapor is condensed with the improved reproducibility because the portion at which the sample is disposed has the temperature lower than its circumferencial portions, particularly the high temperature heated recesses 23, 23'.

Figure 5:
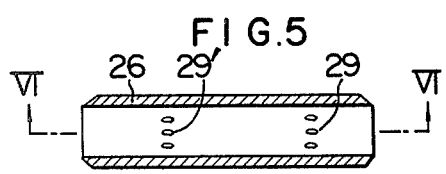
FIG. 5 is a cross section of still another embodiment of a cuvette according to the present invention.
Figure 6:
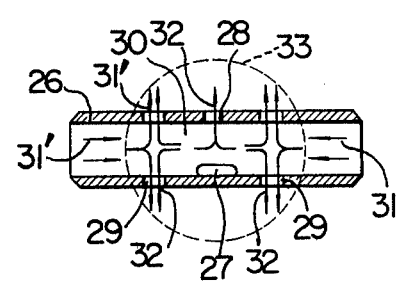
FIG. 6 is a section along a line VI—VI in FIG. 5.

FIG. 5 is a cross section showing still another embodiment of a cuvette according to the present invention. FIG. 6 is a section along a line VI—VI in FIG. 5. A cuvette 26 includes a sample introduction port 28 for introducing a sample 27. A cuvette 26 is provided with a plurality of small holes 29, 29' at its both ends thereof. An arrow 31 shows the flow direction of the carrier gas, and an arrow 32 the flow direction of the atomic vapor from the sample 27. As will be apparent from the flows of the carrier gas and the atomic vapor, the atomic vapor is sealed within the absorption cell section 30. Therefore, the application of a uniform magnetic field 33 so as to cover the absorption cell section 30 allows the improvement in analysis precision and sensitivity. Further, the atomic vapor is prevented from condensation with the improved reproducibility of analysis because the absorption cell section sandwiched by the small holes 29, 29' has the higher temperature than that of the portion at which the sample 27 is disposed.

Figure 7:
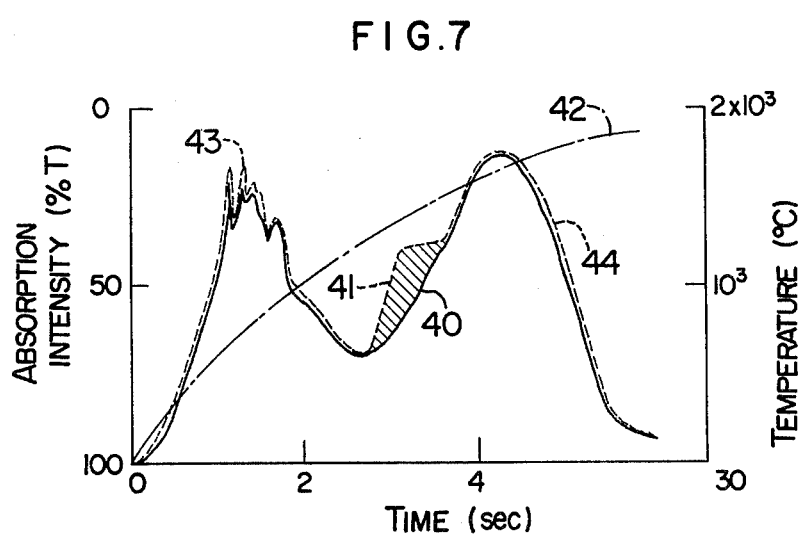
FIG. 7 is a graph showing results of analysis obtained using the flameless atomizer shown in FIG. 1.

FIG. 7 shows analysis results obtained by a Zeeman atomic absorption spectrophotometer in which the flameless analyzer according to one embodiment of the present invention is employed. Prior to the description of FIG. 7, the description will be made about the principles and construction of the Zeeman atomic absorption sectrophotometer in conjunction with FIGS. 8 and 9.

When a resonant incident light beam is applied to the atomic vapor, a transition from a ground state b to excited state a is given as follows:

$$\rho(\underline{e})d\Phi Z |<b|\underline{P}|a>|^2 \cdot |\underline{l}\cdot\underline{e}|^2 N(b) \tag{1}$$

where $\rho(\underline{e})d\omega$ is the intensity of incident light having a polarizing component $\underline{e}$; $|<b|\underline{P}|a>|^2$ the transition probability from the states b to a; N(b) the number of atoms existing in the ground state; $\underline{l}$ the unit vector showing a direction of transition; and $\underline{e}$ the unit vector showing the direction of polarization of the incident light.

The application of a magnetic field H to the atomic vapor determines the direction of transition depending upon the variation $\Delta M$ in magnetic quantum number, that is upon $\Delta M=0$ or $\Delta M=\pm 1$. For $\Delta M=0$, $|\underline{l}\cdot\underline{e}|^2=1$ in the expression (1) with an absorption if the direction of $\underline{e}$ is parallel to that of $\underline{H}$, but $|\underline{l}\cdot\underline{e}|^2=0$ with no absorption if $\underline{e}$ is perpendicular to $\underline{H}$. For $\Delta M=\pm 1$, on the other hand, $|\underline{l}\cdot\underline{e}|^2=0$ with no absorption if $\underline{e}$ is parallel to $\underline{H}$, and $|\underline{l}\cdot\underline{e}|^2=\frac{1}{2}$ with an absorption if $\underline{e}$ is perpendicular H. Further, a greater perturbation of energy occurs for $\Delta M = \pm 1$ than for $\Delta M = 0$. If, therefore, resonant light is caused to be incident which has a sufficiently narrow line profile coinciding with the peak of an absorption line at the magnetic field of zero, then, at the suitable intensity of the magnetic field a phenomenon occurs in which only the oscillating component of the incident light that is parallel to the magnetic field is absorbed and its perpendicular oscillating component is not absorbed. This phenomenon has been experimentally recognized by the present inventors with respect to the atomic absorption lines of metals including fifteen elements.

Figure 8:
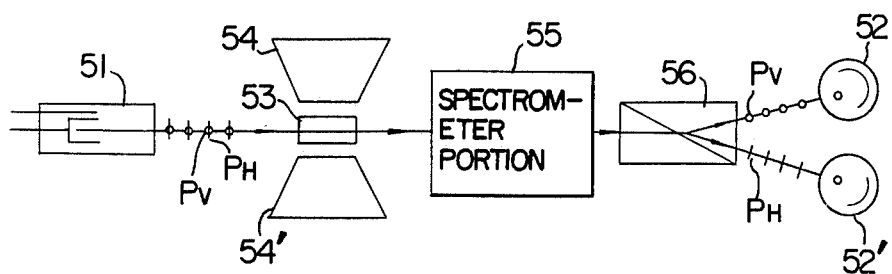
FIG. 8 is a contructive view showing a Zeeman atomic absorption spectrophtometer.

FIG. 8 is a constructive view showing a Zeeman atomic absorption spectrophotometer using the above-mentioned Zeeman atomic absorption analysis. In FIG. 8, a light source portion 51, for example, comprising a hollow cathode lamp, emits light with a single wavelength including two polarizing components $P_V$ and $P_M$ perpendicular to each other. A detector 52 is disposed on the optical path of the light source portion 51 so as to receive the light emitted by it, and includes a light sensor, for example. A sample atomizing device 53 for atomizing a sample to be analyzed is disposed on the optical path between the light source portion 51 and the detector 52. The sample atomizing device 53 is constituted, for example, by the cuvette, cuvette cones, electrodes, and the like as shown in FIG. 1. A magnetic field applying device 54, for example, including a permanent magnet, serves to produce in the sample atomizing device 53 a certain magnetic field the direction of which is perpendicular to the optical path. A spectrometer portion 55 is disposed on the optical path between the sample atomizing device 53 and the detector 52 to effect a spectroscopic analysis of the transmitted light from the sample atomizing device 53. The spectrometer portion 55 comprises a monochrometer including dispersion elements such as diffraction gratings or prisms. A polarization discriminator 56 is disposed at any position on the optical path between the light source portion 51 and the detector 52, for example between the spectrometer portion 55 and the detector 52 as shown in this embodiment as well as between the light source portion and the sample atomizing device 53 or between the sample atomizing device 53 and the spectrometer portion 55. The polarization disc discriminator 56 discriminates the two orthogonal polarizing components $P_V$ and $P_H$ from the light source portion 51 at the respective position, and includes a rotatable polarizer other than a fixed polarizer such as Wollaston prisms shown in the present example, depending upon where the discriminator is disposed.

Figure 9:
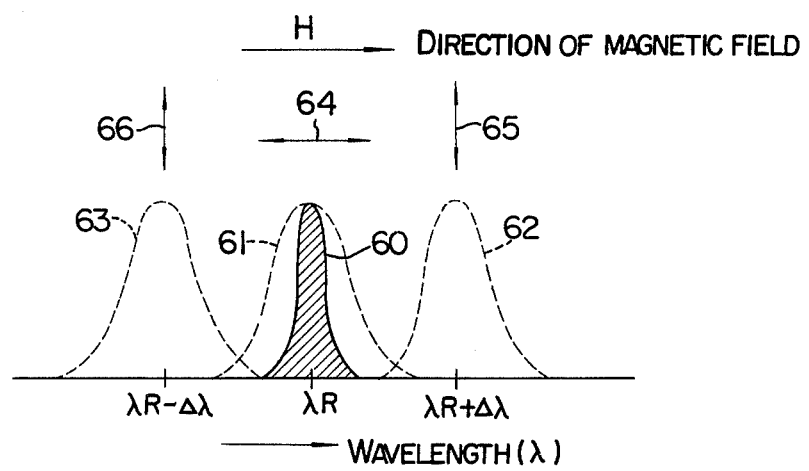
FIG. 9 is diagram for explaining the principle of a Zeeman atomic absorption analyzer.

The sample atomizing device 53 is irradiated with light from the light source portion 51 which has the two polarizing components $P_V$ and $P_H$ perpendicular to each other. In the sample atomizing device 53, the sample to be analyzed is atomized and produces absorption spectral lines, which are divided into three components as shown in FIG. 9 on the basis of a magnetic field H applied perpendicularly to the optical path from the magnetic field applying portion 54. The three components are the first absorption spectral line component 61 having a wavelength substantially coincident with a wavelength $\lambda_R$ of light 60 emitted from the light source portion 51; and the second and third absorption spectral line components having wavelengths $\lambda_R \pm \Delta\lambda$ respectively spaced apart by a predetermined amount of wavelength such as $\pm\Delta\lambda$ from the wavelength $\lambda_R$ of the first absorption spectral line component 61. The first absorption spectral line component 61 is characteristically absorbed by only the polarizing component that includes an oscillation surface 64 parallel to the magnetic field H applied to the sample atomizing device 53, and the second and third absorption spectral line components 62 and 63 are, on the other hand, characteristically absorbed by only the polarizing component that includes oscillation surfaces 65 and 66 perpendicular to the magnetic field H. As shown in FIG. 8, on the other hand, the light emitted from the light source portion 51 includes the polarizing component $P_V$ having an oscillation surface perpendicular to the paper surface, that is, orthogonal to the direction of the magnetic field H, and the polarizing component $P_H$ having an oscillation surface parallel to the paper surface, that is, parallel to the direction of the magnetic field H. Thus, the light source portion 51 emits the two polarizing components $P_V$ and $P_H$ having the oscillation surfaces orthogonal to each other, only the polarizing component $P_H$ having the oscillation surface parallel to the magnetic field H is absorbed by the first absorption spectral line component 61, and the polarizing component $P_V$ having the oscillation surface perpendicular to the direction of the magnetic field H is absorbed neither by the first absorption spectral line component nor by the second and third absorption apectral line components 62 and 63. This is because the polarizing component $P_H$ coincides with the first absorption spectral line 61 in absorption wavelength position and absorption oscillation surface, while the polarizing component $P_V$ coincides in absorption wavelength position with the first absorption spectral line component 61 but does not coincide therewith in absorption oscillation surface, further coinciding in absorption oscillation surface with the second and third absorption spectral lines, respectively, but not coinciding therewith in absorption wavelength position. This means that the polarizing component $P_V$ receives no absorption in any case. Therefore, into the spectrometer portion 55 there are introduced the polarizing component $P_H$ subjected to the absorption by the first absorption spectral line component 61 and having the oscillation surface parallel to the magnetic field H, and the polarizing component $P_V$ not absorbed by any one of the three divided absorption spectral line components and having the oscillation surface perpendicular to the direction of the magnetic field H. The two polarizing components $P_V$ and $P_H$ including the orthogonal oscillation surfaces with the single wavelength $\lambda_R$ selected in the spectrometer portion 55, are discriminated in the polarization discriminator 56 simultaneously or in a time-sharing manner. The use of the Wollaston prisms, for example, as shown in FIG. 8 makes it possible to derive therefrom two polarizing components simultaneously into different directions. Thus, in this case, two detectors 52 are required to receive the respective polarizing components. The use of a rotatable polarizer as the polarization discriminator 56, however allows the time sequential discrimination of the two polarizing components and thus needs only one detector 52 in this case. In each case, a signal difference is measured on the basis of the two polarizing components received by the detector 52 to provide only the atomic absorption without any influence of background absorptions.

The description will next be made with reference to FIG. 7. FIG. 7 shows the results of an analysis in which 10 μl of urine is introduced into the cuvette 1 shown in FIG. 1 as a sample to be analyzed; and cadmium in the urine is analyzed. The cuvette 1 is 4 mm$\phi$ in inner diameter, 6 mm$\phi$ in outer diameter and 35 mm in length. The magnets 6 which sandwich the absorption cell section 12 are disposed with a gap of 9 mm. The measured wavelength is 2288 Å. In FIG. 7, the ordinate shows the absorption intensity (% T) of the sample and the temperature (°C.) of the cuvette 1, and the abscissa shows the time (seconds). A curve 40 shows an absorption due to the polarizing components $P_V$ of the emitted light 60 which has the oscillation surface perpendicular to the direction of the magnetic field, while a curve 41 shows an absorption due to the polarizing component $P_H$ having the oscillation surface parallel to the direction of the magnetic field. A curved line 42 shows a variation in temperature of the cuvette 1 relative to the time. A portion 43 shows a background absorption due to the components of organic materials liable to evaporation in the range of relatively low temperatures. It will be understood that the absorption due to the $P_V$ substantially overlaps with the absorption due to the $P_H$. A portion 44 is a background absorption due to components such as metallic salts evaporated in the range of relatively high temperatures. In this case also, it will be apparent that the absorptions due to the $P_V$ and $P_H$ substantially overlaps with each other. It will be seen from FIG. 7 that the absorption due to the $P_H$ is apparently different from that due to the $P_V$ when the cuvette 1 is heated to a temperature at which cadmium in the urine to be analyzed is evaporated. The value of this difference integrated with respect to the time (hatched portion) is proportional to the concentration of cadmium in the urine.

The flameless atomizer according to the present invention can prevent the condensation or recombination of the atomic vapors from the sample with the improved reproducibility of the analysis.

In the application of the flameless atomizer according to the present invention to the Zeeman atomic absorption analysis, the atomic vapors could be sealed within the absorption cell section with an improvement in precision analysis. That is, the background absorption could be corrected in the absorption degree from 1.7 to 0.002 and completely corrected for the absorption degree below 1.5.

Further, the atomic analyzer according to the present invention could provide an improvement in analysis sensibility, that is, the detection limit at the measurement of the actual sample was 10 to 100 times as great as that in the conventional device.

What we claim is:
1. A flameless atomizer comprising:
    a hollow cuvette including an opening at both ends and a port in a radial direction substantially at its central portion, and made of a conductive material Joule-heated by current flowing therethrough, said cuvette being integrally provided with a projection having a recess in the interior thereof at a position situated in a radial direction substantially at its central portion and substantially opposite to said port;
    electrodes for supporting said cuvette; and
    a device for flowing a protective gas into the interior and exterior of said cuvette, wherein the interior of said cuvette is divided into:
    a sample mount section at which a sample introduced through the port of said cuvette is disposed;
    a light beam path section through which a light beam passes in said cuvette; and
    an absorption cell section at which said light beam path section intersects with atomic vapors generated from the sample disposed in said sample mount section, and a pair of magnets for applying a magnetic field to said absorption cell section limited to a certain area within said cuvette being provided in such a manner that they sandwich said cuvette.

2. A flameless atomizer according to claim 1, wherein;
    a direction along which the atomic vapor is exhausted out of said cuvette; and a direction along which said pair of magnets are facing are made orthogonal to one another.

3. A flameless atomizer according to claim 1, wherein said port has substantially the same inner diameter as that of said recess.

4. A flameless atomizer comprising:
    a hollow cuvette means made of a conductive material which is heated by electric current flowing therethrough, said cuvette means having openings at both ends thereof and a port in a radial direction substantially at the central portion thereof, the interior of said cuvette means being divided into a sample mount section means at which a sample introduced through said port is disposed, a light beam path section means through which a light beam passes in said cuvette means, and an absorption cell section means at which said light beam path section intersects with atomic vapors generated from the sample disposed in said sample mount section means, said sample mount section means comprising an integral projection of said cuvette means, said projection having a recess in the interior thereof at a position situated in a radial direction substantially at the central portion of the cuvette means and substantially opposite said port, said port and said absorption cell section means being arranged for permitting the atomic vapors generated from the sample disposed in said sample mount section means to pass through said absorption cell section and said port to the exterior of said cuvette means and for inhibiting the flow of atomic vapors to other parts of the interior of the cuvette means;
    electrode means for supporting said cuvette and for supplying electric current thereto to enable heating of the cuvette means for generating atomic vapors from the sample; and
    means for flowing a protective gas from the openings of said cuvette means through the interior of said cuvette means to the exterior thereof.

5. A flameless atomizer according to claim 4, wherein said cuvette means provides a temperature distribution enabling the atomic vapors generated from the sample disposed in said sample mount section means to be contained within said absorption cell section means without diffusing to other parts of the interior of said cuvette means.

6. A flameless atomizer according to claim 5, wherein said absorption cell section means is provided with a higher temperature than that of said sample mount section means.

7. A flameless atomizer according to claim 4, further comprising a pair of magnets disposed for sandwiching said cuvette means and for supplying a uniform magnetic field to said absorption cell section means.

8. A flameless atomizer comprising:

a hollow cuvette made of a conductive material which is heated by electric current flowing therethrough, said cuvette including openings at both ends, a port in a radial direction substantially at the central portion thereof, and at least one hole in a radial direction substantially on each of the both sides of the central portion, the electric resistance of said cuvette being smaller at said central portion than at portions thereof provided with said holes, the interior of said cuvette being divided into a sample mount section at which a sample introduced through said port is disposed, a light beam path section through which a light beam passes in said cuvette, and an absorption cell section at which said light beam path section intersects with atomic vapors generated from the sample disposed in said sample mount section, said sample mount section being an integral radial projection of said cuvette having a recess in the interior thereof at a position situated in a radial direction substantially at the central portion of said cuvette and substantially opposite said port;

electrodes for supporting said cuvette and for supplying said cuvette with the electric current;

means for flowing a protective gas from the openings of said cuvette to the holes of said cuvette through the interior of said cuvette; and a pair of magnets for applying a magnetic field to said absorption cell section limited to a certain area within said cuvette and arranged for sandwiching said cuvette.

9. A flameless atomizer according to claim 8, wherein said port has substantially the same inner diameter as that of said recess.

10. A flameless atomizer according to claim 8, further comprising a gas flow adjustment means having a plurality of holes with different diameters being rotatably mounted between said cuvette and said means for flowing said protective gas for enabling stepwise adjustment of the protective gas flow flowed into said cuvette.

11. A flameless atomizer according to claim 10, wherein said gas flow adjustment means is rotatably mounted on at least one of said electrodes.

12. A flameless atomizer according to claim 1, wherein said cuvette is constructed so that the electrical resistance at a portion contacting said sample mount section is smaller than the electrical resistance at a portion near said absorption cell section.

13. A flameless atomizer according to claim 1, wherein said cuvette is constructed so that the absorption cell section is provided with a temperature from the Joule heating which is greater than that temperature provided the sample mount section.

14. A flameless atomizer according to claim 4, wherein said cuvette means is constructed so that the electrical resistance is smaller at a portion contacting said sample mount section means than at a portion near said absorption cell section means.

15. A flameless atomizer according to claim 8, wherein said cuvette is constructed so that the electrical resistance is smaller at a portion contacting said sample mount section than at a portion near said absorption cell section.

* * * * *